United States Patent
Grau et al.

(10) Patent No.: US 6,290,501 B1
(45) Date of Patent: Sep. 18, 2001

(54) SILVER-PALLADIUM ALLOYS FOR PRODUCING A DENTAL PROSTHESIS WHICH CAN BE COVERED WITH DENTAL CERAMIC

(75) Inventors: Franz Josef Grau, Neunkirchen am Brand (DE); Joseph Maria Van Der Zel, Hoorn (NL)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/381,102

(22) PCT Filed: Mar. 23, 1998

(86) PCT No.: PCT/EP98/01682

§ 371 Date: Dec. 2, 1999

§ 102(e) Date: Dec. 2, 1999

(87) PCT Pub. No.: WO98/44894

PCT Pub. Date: Oct. 15, 1998

(30) Foreign Application Priority Data

Apr. 4, 1997 (DE) .............................. 197 13 925

(51) Int. Cl.⁷ .................................... A61C 13/08

(52) U.S. Cl. .................... 433/208; 433/207; 420/463; 420/505

(58) Field of Search .................... 433/208, 207, 433/206; 420/463, 505

(56) References Cited

U.S. PATENT DOCUMENTS

| 3,819,366 | * | 6/1974 | Katz ........................ 420/463 |
| 3,929,475 | * | 12/1975 | Ingersoll .................. 420/505 |
| 5,290,371 | * | 3/1994 | Cameron et al. ......... 148/442 |

FOREIGN PATENT DOCUMENTS

| 3438288 | * | 7/1985 | (DE) . |
| 9200566 | * | 3/1992 | (NL) . |

* cited by examiner

Primary Examiner—Gene Mancene
Assistant Examiner—Melba Bumgarner

(57) ABSTRACT

The invention relates to silver-palladium alloys for the manufacture of dental prostheses which can be faced with dental ceramic.

Because of selected contents of the alloy elements indium, tin and zinc, these cause no discolorations when combined with low-melting dental ceramic with a coefficient of thermal expansion of approx. 16.5 $\mu$m/mK.

7 Claims, No Drawings

SILVER-PALLADIUM ALLOYS FOR PRODUCING A DENTAL PROSTHESIS WHICH CAN BE COVERED WITH DENTAL CERAMIC

BACKGROUND OF THE INVENTION

1. Field of the Invention

The invention relates to silver-palladium alloys for the manufacture of dental prostheses which can be faced with dental ceramic.

2. Description of the Related Art

Fixed and removable dental prostheses are chiefly made of corrosion-resistant, biocompatible precious metal alloys; with the so-called lost wax process, wherein the cast object is often faced with dental ceramic in order to achieve an appearance corresponding to the natural tooth. For this purpose, the alloys must possess specific properties, such as coefficient of thermal expansion, melting range and adhesion, matched to the dental ceramic.

Alloys with a high gold content, such as are described in patent specifications DE-11 83 247 and DE-15 33 233, for example, are particularly well suited to these purposes. Because the price of gold is high and varies considerably, however, in more recent times attempts have increasingly been made to find more reasonably priced alternatives to the alloys with a high gold content. Of the precious metals, palladium is considered for use because of its relatively favourable price, its distinctly reduced density compared to gold and its corrosion and/or mouth resistance, which are comparable to gold.

In addition to a lower price, compared to alloys with a high gold content, palladium base alloys have a higher hardness and strength, a higher solidus temperature brought about by the palladium, a better high temperature resistance and hence, with fired-on alloys, a higher distortion resistance when the ceramic is fired. These alloys are either gold-free or contain only few wt. % of gold. They do, however, react more sensitively to processing errors and are difficult to solder. The palladium content leads to a reduction of the coefficient of thermal expansion, although this may be equalized by the addition of silver.

In respect of their processing behaviour, palladium base alloys containing silver should be classed between the palladium base alloys with a high gold content and the silver-free ones. Compared to silver-free palladium base alloys, because of the silver content, palladium base alloys containing silver can be melted and cast more satisfactorily, have a lighter oxide, exhibit good soldering behaviour, and are also even more reasonably priced.

A dental system which consists of an alloy with a high gold content, a low-melting dental ceramic, and the corresponding solder alloys, was introduced onto the market a few years ago. Compared to the ceramics which had been used up to that time, the low-melting ceramic has a substantially higher coefficient of thermal expansion.

There is an increasing desire to combine this low-melting dental ceramic with a more reasonably priced palladium-silver and/or silver-palladium alloy which can be fired on.

For palladium base alloys which can be fired on, however, a higher coefficient of thermal expansion of the ceramic means a distinct increase in the silver content, to approx. 50 wt. % and above.

The disadvantage of these silver base alloys and/or palladium base alloys with a high silver content is that they discolour the facing ceramic, yellow and/or yellowish green during the firing-on process. The reason for this is the silver which finds its way into the ceramic through diffusion and/or via the vapour phase.

The problems relating to the discoloration of ceramic by silver are known.

Solutions have been found (DE-39 05 987) for palladium-silver alloys which can be fired on for conventional high-melting ceramic with a coefficient of thermal expansion in the range from 14 μm/mK to 15 μm/mK, up to a silver content of 45 wt. % of silver. These alloys are not, however, suitable for firing on low-melting ceramic with a coefficient of thermal expansion of approx. 16.5 μm/mK. The silver content in such fire-on alloys compatible with low-melting ceramic must be increased; the higher silver content generally leads, however, to a higher tendency to discoloration of the dental ceramic by silver, which cannot be suppressed even by the solutions quoted in DE-39 05 987.

DE-PS 25 23 971 describes palladium-silver alloys which contain 0.1 to 0.5% of titanium to suppress the ceramic discoloration. Because of the reactivity of titanium with the atmospheric oxygen and/or the crucible material, this element becomes depleted in the melt relatively quickly, so that the reducing effect on the tendency to discolour is lost if old material (feed channels, casting funnels) is used and if melting conditions are unfavourably selected. Titanium also causes a strong adhesion of the embedding compound on the surface of the cast object, which makes dis-embedding and finishing more difficult and more time-consuming.

U.S. Pat. No. 4,350,526 describes palladium-silver alloys which do not have a discolouring effect on dental ceramic because of an addition of 0.1 to 1.0% of silicon. Silicon is insoluble in both palladium and silver. Palladium and silicon also form intermetallic phases so that great brittleness of the alloy and casting fragility can occur.

Like titanium, silicon promotes the reaction with ceramic materials, so that strong adhesion of the embedding compound on the cast object occurs with these alloys also.

According to DE-PS 29 42 373, additions of 0.01 to 5% of silicon, boron and/or germanium should suppress the silver discoloration in dental alloys with 30 to 50% gold contents. Germanium alone cannot, however, bring about such effects in gold-free or low-gold palladium alloys.

NL 9200566 describes fire-on palladium-silver alloys which may also contain indium, tin and zinc in addition to further alloy constituents-. These alloys are provided for facing with conventional high-melting ceramic with a coefficient of thermal expansion around 14.5 μm/mK. In practice, however, it has emerged that these alloys cause strong discolorations on dental ceramic, particularly of the more recent low-melting type with a coefficient of thermal expansion around 16.5 μm/mK.

BRIEF SUMMARY OF THE INVENTION

The object of the invention was therefore to develop silver-palladium alloys for the manufacture of fixed and removable dental prostheses which can be faced with low-melting dental ceramic with a coefficient of thermal expansion of approx. 16.5 μm/mK onto which such discoloration-sensitive dental ceramics may be fired without identifiable colour changes and which can easily be dis-embedded from the conventional embedding compounds without the remaining properties of the silver-palladium alloys changing significantly.

It has now been found that these conditions are met by silver-palladium alloys which consist of 45–65 wt. % of Ag, 30–45 wt. % of Pd, 0–5 wt. % of Au, 0–5 wt. % of Pt, 0–3 wt. % of Ge, 0–3 wt. % of Cu, 0–7 wt. % of Ga, 0–5 wt. % of Co, 0–1 wt. % of Mo, 0–1 wt. % of Ru, 0–1 wt. % of Re, 0–1 wt. % of Ir and 0 to 6 wt. % in each case of In, Sn and Zn, wherein all constituents add up to 100%, and which are characterized in that either with an In content of 0–1 wt. % the Sn content is 1–6 wt. % and the Zn content 2–6 wt. % at the same time or with an In content of 3–6 wt. % the Sn content is 0–4 wt. % and the Zn content 4–6 wt. % at the same time.

DETAILED DESCRIPTION OF THE INVENTION

The invention therefore provides the use of silver-palladium alloys as characterized above for the manufacture of dental prostheses which can be faced with low-melting dental ceramic with a coefficient of thermal expansion of approx. 16.5 μm/mK.

The invention also provides the use of silver-palladium alloys as characterized above and low-melting dental ceramic with a coefficient of thermal expansion of approx. 16.5 μm/mK for the manufacture of discoloration-free dental prostheses faced with dental ceramic.

The invention further provides fixed and removable dental prostheses in which a substructure comprising a silver-palladium alloy as characterized above is faced with a low-melting dental ceramic with coefficient of thermal expansion of approx. 16.5 μm/mK.

The alloys according to the invention have a coefficient of thermal expansion which is between 16.4 and 17.1 μm/mK. They are therefore particularly compatible with low-melting dental ceramic with a coefficient of thermal expansion of approx. 16.5 μm/mK.

It has surprisingly been shown that in respect of the alloy composition there are ranges in which no discoloration of the dental ceramic and/or a distinct reduction of the yellow/green discoloration of dental ceramics compared to traditional silver-palladium alloys takes place.

This applies in both cases, if either with a 0–1 wt. % In content the Sn content is 1–6 wt. % and the Zn content 2–6 wt. % at the same time or with a 3–6 wt. % In content the Sn content is 0–4 wt. % and the Zn content 4–6 wt. % at the same time.

In addition to silver and palladium these alloys chiefly contain the elements indium, tin and zinc in the quantities quoted. The alloys according to the invention may optionally further contain the elements gold, platinum, germanium, gallium, indium, cobalt, copper and molybdenum in the quantities quoted. The elements serve to adjust the mechanical properties such as strength, hardness, castability and melting range. Ruthenium, rhenium and/or iridium may be co-alloyed in the concentration ranges quoted as particle fining additives.

The alloys according to the invention are biocompatible. It was possible to dispense with the use of toxic and allergenic elements such as cadmium or nickel.

The indium content in combination with the zinc and tin content demonstrated a decisive influence on the tendency to discolour. Intensive green/yellow discolorations were discernible with indium contents in the range round 2 wt. %. With a low indium content up to 1 wt. % max. and at the same time tin contents of 1–6 wt. %, a minimum as regards tendency to discolour was discernible when the zinc content was 2–6 wt. %. Dental alloys with indium contents below 1 wt. %, and tin and zinc contents of 3 to 5 wt. %, were shown to be discoloration-free. In this composition range, the silver is so firmly bound by the other alloying elements, including in regions close to the surface, that a discoloration through diffusion of the silver and/or a discoloration of the dental ceramic via possible silver from the vapour phase is prevented.

Alloys according to the invention with a low indium content preferably contain 50–60 wt. % of Ag, 32–45 wt. % of Pd, 0–1 wt. % of In, 3–5 wt. % of Sn and 3–5 wt. % of Zn.

Indium-free alloys which contain 55–57 wt. % of Ag, 35–38 wt. % of Pd, 3–5 wt. % of Sn and 3–5 wt. % of Zn are particularly preferred.

It was surprisingly demonstrated in the tests that with indium contents of 3–6 wt. % there is a second range when the zinc content is 4–6 wt. % and the tin content 0–4 wt. %. A barrier against silver diffusion is formed in this composition range. It is, however, important that the indium content is not below 3 wt. % and the tin content does not exceed 4 wt. %, as otherwise the silver diffusion barrier is weakened and an increase in the tendency to discolour is discernible. In this respect, alloys with tin contents of 2 wt. % max. and an indium content of at least 3 wt. % are more favourable, if the alloy simultaneously contains at least 4 wt. % of zinc.

Corresponding alloys which contain 50–60 wt. % of Ag, 32–45 wt. % of Pd, 3–6 wt. % of In, 0–2 wt. % of Sn and 4–6 wt. % of Zn are preferred.

Those alloys which contain 50–55 wt. % of Ag, 38–42 wt. % of Pd, 3–5 wt. % of In, 0.5–2 wt. % of Sn and 4–5 wt. % of Zn are particularly preferred.

The silver-palladium alloys to be used according to the invention may be processed in known manner with techniques and auxiliary substances conventional for this purpose,into fixed or removable dental prostheses faced with dental ceramic. By the lost wax process, for example, they are cast into a substructure which is then faced by firing-on low-melting dental ceramic.

Table 1 shows the composition and properties of a number of alloys according to the invention. They are distinguished by an outstanding castability and a problem-free faceability with known, low-melting dental ceramics with a coefficient of thermal expansion of approx. 16.5 μm/mK.

The colour of the facing ceramic on the alloys after firing was determined by reflection measurement, by means of a spectrophotometer in comparison with a standard sample (Palliag NF IV). In the reflection measurement the sample is illuminated with diffuse light and observed at an angle of observation of 2 degrees. The results are summarized in Table 2 (CIEL system, illuminant D 65). The a-value describes the position on the green/red axis (negative=green, positive=red), the b-value the position on the blue/yellow axis (blue negative, yellow positive). Table 2 does not contain the absolute colour values, but the deviations of the colour values for the ceramic facing on the various alloys from the standard sample (Δ-values). In the alloys according to the invention, a distinct reduction of the yellow/green discoloration was measurable compared to the standard alloy. When crowns and bridges produced from alloys according to the invention and faced were observed visually, no discoloration of the ceramic could be observed.

TABLE 1

Alloy compositions and mechanical properties
Composition and properties of a number of alloys
according to the invention
CTE = coefficient of thermal expansion

| Alloy | Melting range (° C.) | Hardness after ceramic firing (HV 5) | CTE between room temp. and 600° C. (μm/mK) | 0.2 proof limit (MPa) | Elongation at break (%) |
|---|---|---|---|---|---|
| 50 Ag/39.9 Pd/4 Zn/1 In/ 5 Sn/0.1 Ir | 1028/1105 | 220 | 16.6 | 598 | 6.0 |
| 51.8 Ag/39.9 Pd/4 Zn/3 In/ 1 Sn/0.1 Au/0.2 Ru | 1065/1145 | 205 | 16.5 | 572 | 6.3 |
| 54.8 Ag/36.7 Pd/1 Ga/1.2 Ge/ 3 Zn/1 Sn/2 Co/0.3 Ru | 1015/1097 | 176 | 16.7 | 536 | 5.7 |
| 52.8 Ag/39.9 Pd/4 Zn/3 In/ 0.1 Au/0.2 Ru | 1098/1173 | 201 | 16.6 | 545 | 6.7 |
| 55.8 Ag/36.9 Pd/4 Zn/3 Sn/ 0.3 Ru | 1102/1182 | 207 | 16.9 | 588 | 5.8 |
| 56 Ag/36.9 Pd/4 Zn/3 Sn/ 0.1 Ir | 1095/1188 | 212 | 17.1 | 590 | 6 |
| 51.8 Ag/39.9 Pd/4 Zn/4 In/ 0.1 Au/0.2 Ru | 1075/1165 | 214 | 16.8 | 595 | 6.0 |
| 48.5 Ag/42.2 Pd/3 Zn/1 In/ 5 Sn/0.1 Ir/0.2 Re | 1047/1142 | 188 | 16.4 | 558 | 6.7 |
| 56 Ag/1 Pt/34.9 Pd/1 Au/ 3 Zn/4 Sn/0.1 Ir | 1073/1167 | 197 | 17.0 | 572 | 6.3 |
| 52.8 Ag/39.2 Pd/4 Zn/3 In/ 0.7 Sn/0.1 Au/0.2 Ru | 1072/1158 | 201 | 16.6 | 588 | 5.8 |

TABLE 2

Spectrophotometer results
Results of the colour measurements on a number
of alloys according to the invention and the comparative alloy

| | Alloy | Δa | Δb |
|---|---|---|---|
| Standard sample (Palliag NF IV) | 52 Ag/39.9 Pd/4 Zn/2 In/2 Sn/0.1 Ir | — | — |
| | 50 Ag/39.9 Pd/4 Zn/1 In/5 Sn /0.1 Ir | 0.48 | −2.31 |
| | 51.8 Ag/39.9 Pd/4 Zn/3 In/1 Sn/0.1 Au/ 0.2 Ru | 1.04 | −5.37 |
| | 54.8 Ag/36.7 Pd/1 Ga/1.2 Ge/3 Zn/ 1 Sn/2 Co/0,3 Ru | 0.39 | −1.97 |
| | 52.8 Ag/39.9 Pd/4 2n/3 In/0.1 Au/ 0.2 Ru | 0.55 | −2.37 |
| | 55.8 Ag/36.9 Pd/4 Zn/3 Sn/0.3 Ru | 0.82 | −4.81 |
| | 56 Ag/36.9 Pd/4 Zn/3 Sn/0.1 Ir | 1.02 | −5.32 |
| | 51.8 Ag/39.9 Pd/4 Zn/4 In/0.1 Au/ 0.2 Ru | 0.65 | −2.73 |

TABLE 2-continued

Spectrophotometer results
Results of the colour measurements on a number
of alloys according to the invention and the comparative alloy

| Alloy | Δa | Δb |
|---|---|---|
| 48.5 Ag/ 42.2 Pd/3 Zn/1 In/5 Sn/ 0.1 Ir/0.2 Re | 0.58 | −3.15 |
| 56 Ag/1 Pt/34.9 Pd/1 Au/3 Zn/4 Sn/ 0.1 Ir | 0.96 | −4.41 |
| 52.8 Ag/39.2 Pd/4 Zn/3 In/0.7 Sn/ 0.1 Au/0.2 Ru | 0.93 | −4.65 |

What is claimed is:

1. An alloy for the manufacture of dental prostheses faced with low-melting dental ceramic having a coefficient of thermal expansion of approximately 16.5 μm/mK., the alloy consisting of:

45–60 wt. % of Ag;
30–45 wt. % of Pd;
0–5 wt. % of Au;
0–5 wt. % of Pt;
0–3 wt. % of Ge;
0–3 wt. % of Cu;
0–7 wt. % of Ga;
0–5 wt. % of Co;
0–1 wt. % of Mo;
0–1 wt. % of Ir;
0–1 wt. % of Ru;
0–1 wt. % of Re;
0–1 wt. % or 3–6 wt. % of In;

0–6 wt. % of Sn; and

0–6 wt. % of Zn, with the proviso that, when the In content is from 0–1 wt. %, the Sn content is from 1–6 wt. % and the Zn content is from 2–6 wt. %, and with the proviso that, when the In content is from 3–6 wt. %, the Sn content is from 0–4 wt. % and the Zn content is from 4–6 wt. %.

2. The alloy according to claim 1, wherein the alloy contains from 50–60 wt. % of Ag; from 32–45 wt. % of Pd; from 0–1 wt. % of In; from 3–5 wt. % of Sn; and from 3–5 wt. % of Zn.

3. The alloy according to claim 2, wherein the alloy contains from 55–57% of Ag; from 35–38 wt. % of Pd.

4. The alloy according to claim 1, wherein the alloy contains from 50–60 wt. % of Ag; from 32–45 wt. % of Pd; from 3–6 wt. % of In; from 0–2 wt. % of Sn, and from 4–6 wt. % of Zn.

5. The alloy according to claim 4, wherein the alloy contains from 50–55 wt. % of Ag; from 38–42 wt. % of Pd; from 3–5 wt. % of In; from 0.5–2 wt. % of Sn; and from 4–5 wt. % of Zn.

6. A discoloration-free dental prosthesis, comprising:

the alloy according to claim 1; and a low-melting dental ceramic, having a coefficient of thermal expansion of approximately 16.5 $\mu$m/mK, facing the alloy.

7. A fixed or removable dental prosthesis, comprising:

the alloy according to claim 1; and a low-melting dental ceramic having a coefficient of thermal expansion of approximately 16.5 $\mu$m/mK, facing the alloy.

* * * * *